(12) United States Patent
Kotani et al.

(10) Patent No.: US 7,211,567 B1
(45) Date of Patent: May 1, 2007

(54) COMPOSITION FOR PREVENTING AND TREATING TYPE I ALLERGY

(75) Inventors: Mayumi Kotani, Kobe (JP); Akihito Fujita, Takatsuki (JP); Motonobu Matsumoto, Takatsuki (JP)

(73) Assignees: Sunstar, Inc., Osaka (JP); Sunstar Suisse S.A., Ecublens (CH)

( * ) Notice: Subject to any disclaimer, the term of this patent is extended or adjusted under 35 U.S.C. 154(b) by 0 days.

(21) Appl. No.: 09/937,365

(22) PCT Filed: Mar. 24, 2000

(86) PCT No.: PCT/JP00/01801

§ 371 (c)(1),
(2), (4) Date: Jan. 18, 2002

(87) PCT Pub. No.: WO00/57888

PCT Pub. Date: Oct. 5, 2000

(30) Foreign Application Priority Data

Mar. 26, 1999 (JP) ................... 11-084395
Apr. 30, 1999 (JP) ................... 11-123633
Jun. 21, 1999 (JP) ................... 11-173731

(51) Int. Cl.
*A61K 31/7048* (2006.01)

(52) U.S. Cl. .................. 514/25; 424/439; 514/460

(58) Field of Classification Search ........... 424/400, 424/489, 439, 464, 451; 514/460, 25
See application file for complete search history.

(56) References Cited

U.S. PATENT DOCUMENTS 4,808,574 A * 2/1989 Brekhman et al. ............ 514/23
5,478,579 A * 12/1995 Sawruk ....................... 424/535

2002/0068094 A1 * 6/2002 Aga et al. .................... 424/725

FOREIGN PATENT DOCUMENTS

| | | |
|---|---|---|
| DE | 195 44 905 A1 | 6/1997 |
| EP | 0 633 022 A2 | 1/1995 |
| GB | 2 198 041 A | 6/1988 |
| JP | 09-255583 | 9/1997 |
| JP | 11029561 A * | 2/1999 |
| WO | WO 98/42188 | 10/1998 |
| WO | WO9842188 * | 10/1998 |

OTHER PUBLICATIONS

H. Fukumoto et al., Anti-anaphylactic Effects of the Principal Compounds from the White Petals of *Impatiens balsamina* L., Phytotherapy Research, vol. 10, 1996, pp. 202-206.*

Fukumoto et al., Antianaphylactic Effects of the Principal Compounds from the White Petals of *Impatiens balsamina* L.), 1996, Phytotherapy Research, vol. 10, 202-206.*

(Continued)

*Primary Examiner*—Neil S. Levy
(74) *Attorney, Agent, or Firm*—Knobbe Martens Olson & Bear LLP

(57) ABSTRACT

A food composition for preventing type I allergy, a pharmaceutical composition for preventing or treating type I allergy and an external preparation for skin for preventing or treating type I allergy.

20 Claims, 2 Drawing Sheets

OTHER PUBLICATIONS

K. Ishiguro et al., Antipruritic Effect of Flavonol and 1,4-Naphthoquinone Derivatives from *Impatiens balsamina* L., *Phytotherapy Research*, vol. 11, 1997, pp. 343-347.

H. Fukumoto et al., Antianaphylactic Effects of the Principal Compounds from the White Petals of *Impatiens balsamina* L., *Phytotherapy Research*, vol. 10, 1996, pp. 202-206.

T. Tsuruga et al., Biologically Active Constituents of *Magnolia salicifolia*: Inhibitors of Induced Histamine Release from Rat Mast Cells, *Chem. Pharm. Bull.*, vol. 39, No. 12, 1991, pp. 3265-3271.

E. Middleton, Jr., Effect of Flavonoids on Basophil Histamine Release and Other Secretory Systems, *Plant Flavonoids in Biology and Medicine: Biochemical, Pharmacological, and Structure-Activity Relationships*, 1986, pp. 493-506.

* cited by examiner

COMPOSITION FOR PREVENTING AND TREATING TYPE I ALLERGY

This is the U.S. National Phase under 35 U.S.C.§371 of International Application PCT/JP00/01801, filed Mar. 24, 2000, which claims priority of Japanese Applications JP 1999-84395, filed Mar. 26, 1999, JP 1999-123633, filed Apr. 30, 1999, and JP 1999-173731, filed Jun. 21, 1999 (all of which are herein incorporated by reference).

TECHNICAL FIELD

The present invention relates to compositions comprising kaempferol-3-glucoside for preventing or treating type I allergy, and more particularly to a food composition for preventing type I allergy, a pharmaceutical composition for preventing or treating type I allergy and an external preparation for skin for preventing or treating type I allergy.

BACKGROUND ART

In recent years it has been reported that various substances contained in plants have antiallergic actions. For example, it has been reported that kaempferol, which is a type of flavonoid, has type I allergy suppression effect. However, this effect is not sufficient. The type I allergy suppression effect of kaempferol-3-glucoside (also referred to as 'astragalin'), which is a glycoside of kaempferol and is represented by undermentioned general formula (1), on the other hand, has not previously been found.

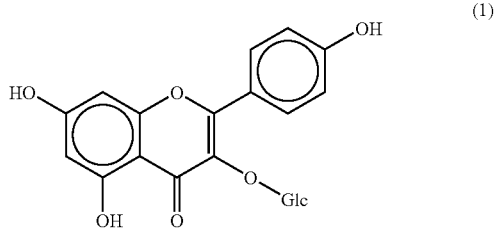

(1)

DISCLOSURE OF INVENTION

An object of the present invention is to provide a food composition, a pharmaceutical composition and an external preparation for skin, which comprises as an active ingredient a compound surprising effective at suppressing type I allergy and its symptoms, and thus having an excellent preventative or therapeutic effect on type I allergy.

The inventors found, during type I allergy screening, that kaempferol-3-glucoside (astragalin) has an excellent action of suppressing passive cutaneous anaphylaxis in mice. The present invention was accomplished based on this finding.

The inventors discovered, during atopic dermatitis screening, that astragalin is capable of suppressing atopic dermatitis and can also suppress a rise in serum IgE level, and also discovered that astragalin suppresses the symptoms of pollinosis. The present invention thus provides the items listed below:

Item 1. A composition for preventing or treating type I allergy and diseases associated with type I allergy, comprising kaempferol-3-glucoside as an active ingredient.

Item 2. The composition according to item 1, wherein the composition is a food composition for preventing type I allergy and diseases associated with type I allergy.

Item 3. The composition according to item 1, wherein the composition is a pharmaceutical composition for preventing or treating type I allergy and diseases associated with type I allergy.

Item 4. The composition according to item 1, wherein the composition is an external preparation for skin for preventing or treating type I allergy and diseases associated with type I allergy.

Item 5. The composition according to item 1, wherein the diseases associated with type I allergy are atopic diseases.

Item 6. The composition according to item 1, wherein the disease associated with type I allergy is pollinosis.

Item 7. A method for preventing or treating type I allergy and diseases associated with type I allergy by ingesting or administering an effective amount of kaempferol-3-glucoside.

Item 8. The method according to item 7, wherein the diseases associated with type I allergy are atopic diseases.

Item 9. The method according to item 7, wherein the disease associated with type I allergy is pollinosis.

DETAILED DESCRIPTION OF THE INVENTION

Figure 1:
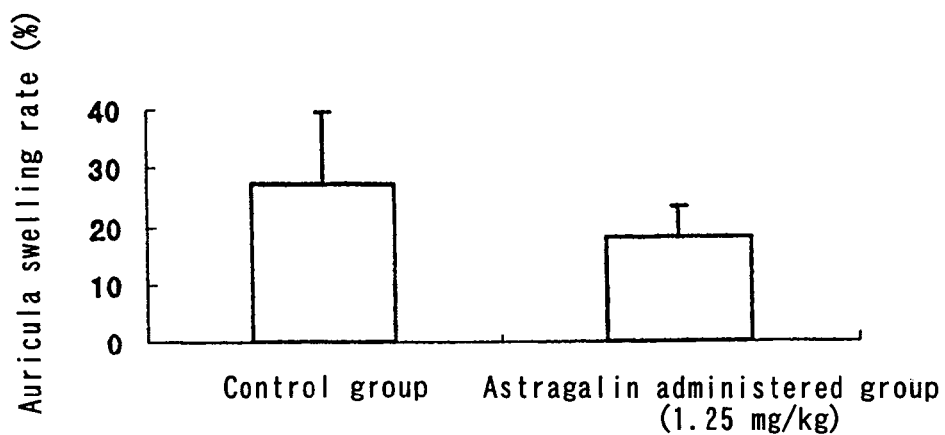
FIG. 1 shows the suppressive effect of kaempferol-3-glucoside (astragalin) on passive cutaneous anaphylaxis (PCA) in mice (Experimental Example 1)

A composition comprising kaempferol-3-glucoside for preventing or treating type I allergy according to the present invention can be used as a food composition, a pharmaceutical composition or an external preparation for skin.

1. Food Composition

The food composition of the present invention can be used in the prevention of type I allergy and allergic diseases associated with type I allergy.

Examples of allergic diseases associated with type I allergy include atopic dermatitis, bronchial asthma, allergic rhinitis and other atopic diseases (sometimes referred to merely as 'atopy'), allergic contact dermatitis, pollinosis and urticaria. Of these, the food composition of the present invention is preferably used for preventing pollinosis and atopic diseases (in particular atopic dermatitis).

Astragalin is capable of suppressing a rise in serum IgE level, and hence the food composition of the present invention can also be used for suppressing a rise in serum IgE level.

The serum IgE level suppressing food of the present invention can be applied to all diseases accompanied by a rise in serum IgE level without limitation. Examples of diseases accompanied by a rise in serum IgE level include atopic dermatitis, bronchial asthma, allergic rhinitis, food allergies, pollinosis and urticaria.

The kaempferol-3-glucoside (astragalin) comprised in the food composition of the present invention can be synthesized by known methods. Moreover, astragalin is contained in various plants, and hence plant-derived astragalin may also be used. In the case that a plant is the source, either the purified astragalin or an extract comprising astragalin may be used as the astragalin.

Preferable examples of plants containing large amounts of astragalin include persimmon (*Diospyros kaki*) leaves, amachazuru (*Gynostemma pentaphylla*), gymnema, guava (*Psidium guajava*), kuko (*Lycium chinense*), striped bamboo (*Sasa veitchii*), jasmine (*Jasminum officinale*), sugina (*Equisetum arvense* L.), dokudami (*Houttuynia cordata*), hatomugi (*Coix mayuen* Roman.), loquat (*Eriobotrya japonica*) leaves, sen-cha, and tien-cha.

Other examples of plants containing large amounts of astragalin include the following: *Securigera securidacea* (L.) Deg. et Dorfl. (Fabaceae) seed, *Vahlia capensis*, Moroheiya (Vietnamese *Corchorus olitorius* L. (Tiliaceae)), *Alsophila spinulosa* (Hook) Tryon., *Camellia sinensis* O. Kuntze, *Ochradenus baccatus.*, Milkvetch root (Radix Astragali), *Glycyrrhiza uralensis* Ficsh (Leguminosae), zhongfeng naomai tong oral liquid, *Mussaenda arcuata* Lam. ex Poiret, *Eupatorium cannabinum* L., persimmon (*Dispyros kaki*), *Wikstroemia indica*, *Dianthus barbatus* cv. ('China Doll', Caryophyllaceae), *Anodendron affine* Durce., *Coronilla varia* L., *Magnolia fargesii*, *Ailanthus altissima*, *Aralia continentalis* kitagawa (Araliacene), *Tribulus terrestris* Linn, *Ochna obtusata* (Ochnacene), *Hedera helix* L. (Araliaceae), *Impatiens balsamina* L., *Circaea lutetiana* ssp. *Canadensis*, *Herniaria mauritanica* Murbeck, *Glycyrrhiza globra*, *Glycyrrhiza echinata*, *Glycyrrhiza pallidiflora*, *Glycyrrhiza foctida*, *Aconitum pseudolaeve* var. *erectum*, saffron (*Crocus sativus*), *Cucurbita pepo* L., *Pulmonaria officinalis*, *Potentilla anserina* L. (Rosaceae), *Phyllanthus emblica*, *Querucus pedunculata*, *Rumex cyprius*, *Terminalia bellerica*, *Terminalia chebula*, *Terminalia horrida*, *Corchorus olitorius* L., *Polygonum aviculare*, *Kummerowia striata*, *Morus alba* L., *Agrimonia eupatoria*, *Drosera rotundifolia* L. (Droseraceae), *Lysimachiae herba*, *Lysimachia chiristinae* var. *typica*, and *Scolymus hispanicus*.

Other examples include the following plants: *Euonymus* species, *Morus insignis*, *Pyrrosia lingua*, *Apoynum venetum* L., *Poacynum hendersonii* (Hook f.) woodson, *Hedyosmum bonplandianum*, H.B.K. (Chloranthaceae), *Carthamus tinctorius*, *Orostachys japonicus*, *Eucommia ulmoides*, *Polyganum cognatum*, *Erythroxylon myrsinites*, *Mussaenda arcuata*, *Escallonia illinita* Presl., *Helichrysum italicum* G. Don (compositae), *Artemisia annua* L., *Astragalus aitosensis*, *Eupatorium guayanum*, *Helichrysum* species, *Diplazium nipponieum* Tagawa, *Festuca Asgentina*, *Athaea officinalis*, *Tinospora malabarica* Miers, *Coronilla varia* L., Chinese tallow tree (*Sapium sebiferum*), fern *Lygodium flexuosum*, *Asanthus*, *Helichrysum graveolens*, *Arabidopsis thaliana* (L.) Heynh., *Cleome droserifolia*, *Helichrysum sanguineum*, *Helichrysum noeanum* Boiss. (Asteraceae), *Epilobium fleischeri*, *Epilobium adenocaulon*, *Epilobium palustre*, *Astrantia major* L., *Hirschfeldia incana.*, *Digitalis lanata*, *Quercus ilex* L., *Smyrnium perfoliatum*, *Smyrnium creticum*, *Smyrnium rotundifolium*, *Ascarina lucida*, *Helichrysum armenium*, *Maclura pomifera* fruit, *Castanea sativa* Mill, *Tussilago farfara* L., *Anchusa officinalis* L., *Cyathea contaminans* Copel, *Solidago virgaurea* L. var. *leiocarpa* (Benth.) A., *Helichrysum Plicatum* DC. ssp. *polyphyllum* (Ledeb.) Davis-Kupicha, *Choisya ternata* Kunth, *Pteridium aquilinum* var. *Latiusculum* IV., and *Isopyrum thalictroides* L. II.

In addition to the above, the following plants also contain astragalin: *Cassia obtusifolia* L., *Helichrysum plicatum* DC, *Convallaria maialis*, *Falcaria vulgaris* Bernh. (Umbelliferae), Umckaloabo, *Clitoria ternatea* L., Larix needles, *Helichrysum orientale* (L.) Gaertner, *Ageratum mexicanum* Sims. (Compositae), *Ribes nigrum*, *Mangifera indica*, *Synadenium carinatum*, *Papaver radicatum*, *Loropetalum Chinense*, Scot pine (*Pinus sylvestris* L.), *Cuscuta australis* R. Br., *Allium victorialis* L., *Sapium japonicum* (Euphorbiaceae), *Euphorbia pekinensis*, *Viburnum awabuki*, *Ilex centrochinensis*, *Polygonum aviculare*, *Atractylodes lancea* DC. (Composieae), carthami flos., *Lonicera japonica*, *Glycyrrhiza uralensis* Fisch., *Althaea officinalis* var. *russalka*, *Alhagi persarum* Boiss. and Buhse., Quercus-ilexl, Mulberry (*Morus alba*) leaves, Hippophae-phamnoides, *Astragalus membranaceous* Bge. var. *mogholicus* (Bge.) Hsiao, Fengrutong granule, *Cirsium setosum*, *Analphalis contorta* Hooker, beggarticks (Bidens parviflora), tormentil, *Apocynum hendersonii* Hook. F., *Astragalus dipelta*, *Gliricidia sepium*, *Cyclachaena xanthifolia*, *Helichrysum noeanum* Boiss. (Asteraceae), *Persica vulgaris*, *Rhododendron micranthum* Turcz, *Viburnum urceolatum*, *Salix caprea*, *Salix alba*, *Orobus vernus*, *Lepidium draba*, *Lepidium ruderale*, *Onobrychis pulchella*, *Onobrychis tanaitica*, *Onobrychis arenaria*, *Asclepias incarnata*, *Orchis sambucina*, *Astragalus ammodendron*, *Syringa vulgaris* leaves, *Picea obovata* needles, *Osmunda japonica*, *Potentilla tanacerifolia*, *Astragalus flexus*, *Aesculus indica.*, *Doronicum macrophyllum*, *Doronicum oblongifolium*, *Astragalus testiculatus*, Pteridaceae, *Onobrychis vassiltschenkoi*, *Fraxinus raibocarpa*, *Boehmeria tricuspis*, *Boehmeria holosericea*, Komarov's oxytropis, *Trifolium hybridum*, *Trifolium ambiguum*, *Delphinium*, *Campanula hypopolia*, *Homogyne*, *Pteridium aquilinum*, *Vaccinium myrtillus*, *Oxytropis lanata*, *Sempervivum ruthenicum*, *Cucurbita maxima*, *Anodendron affine*, *Quercus pontica*, *Baccharis angustifoia*, *Berlandiera pumila*, *Padus avium*, *Onobrychis kachetica*, *Onobrychis inermis*, *Sempervivum ruthenicum*, *Lupinus luteus*, *Alcea nudiflora*, *Rhus coriaria*, *Gymnadenia conopea*, *Spiraea media*, *Adiantum capillus-veneris*, *Adiantum cuneatum*, *Corydalis lutea*, *Ononis arvensis*, *Paeonia arborea*, *Paeonia suffruticosa*, *Bauhinia purpurea*, *Sorbus pendula*, *Arnica* species, and *Nyctanthes arbor-tristis*.

The astragalin content of the food composition of the present invention can be selected from a wide range without limitation, so long as the intended effects are obtained. The astragalin content is generally in a range of about 0.00001 to 80% relative to the total weight of the composition (here and hereinafter '%' means 'weight %'), preferably about 0.0001 to 70%.

The food composition of the present invention can be prepared by mixing astragalin into a carrier comprising food ingredients, additives and the like, and then following conventional methods for the food form to be made.

The food composition of the present invention can be prepared in any of various forms. Examples include liquid beverages such as juices, soft drinks and teas; powdered beverages such as powdered juices and powdered soups; confectionery such as chocolates, candies, chewing gums, ice creams, jellies, cookies, biscuits, corn flakes, chewable tablets, gummi candies, wafers and rice crackers; seasonings such as dressings and sauces; breads; noodles; konnyaku (arum root paste); fish paste products such as kamaboko; and furikake (a seasoned powder for sprinkling on cooked rice).

The food composition of the present invention may comprise food ingredients and additives usually incorporated into foods of the form to be made. Examples of additives include sweeteners, colorants, antioxidants, vitamins and aromatics.

The food composition of the present invention may also comprise plants such as crude drugs and herbs (chamomile, ginger, rose hip etc.) or extracts thereof.

The food composition of the present invention can also be used as a food ingredient used in the preparation of any food. When the food composition of the present invention is used as such a food ingredient, it may be added to a food product that has already been prepared, for example a commercially available beverage.

The intake amount of the food composition of the present invention for preventing type I allergy is suitably selected in accordance with conditions such as the form of the food and the age and sex of the person ingesting the food, but is generally such that the daily intake of astragalin per kg of body weight is in a range of about 0.025 to 3 mg, preferably about 0.05 to 1.5 mg. The food may be ingested either once per day or in 2 to 4 divided amounts per day.

The food composition of the present invention has a type I allergy preventive action, and can be used as a health food, a functional food, a nutritional supplement food, a food for specified health use, a food for sick persons, and so on.

For example, the food composition of the present invention may be ingested with the purpose of prevention by a person who is at risk of developing pollinosis, such as a person who has previously experienced pollinosis. In such a case, the food composition may be ingested throughout the year, but is preferably ingested starting a few weeks before the start of the pollen season.

Moreover, the food composition of the present invention may be ingested with the purpose of preventing atopy by, for example, a person who has previously experienced atopy, a person predisposed to allergies, an infant or the like.

The food composition of the present invention can also be used as a livestock feed or a pet food. The food composition may be in any form conventionally used for livestock feeds or pet foods. The food composition can be prepared by mixing astragalin together with food ingredients and additives usually incorporated into livestock feeds or pet foods, and then following conventional methods for the form to be made.

Provided the intended effects of the present invention are obtained, the astragalin content and the intake amount of the livestock feed or pet food can be selected without limitation in accordance with the form thereof, the type of livestock or pet, and so on, and referring to the case of a food composition for human consumption described above.

2. Pharmaceutical Composition

The pharmaceutical composition of the present invention can be used in the prevention or treatment of type I allergy and allergic diseases associated with type I allergy.

Examples of allergic diseases associated with type I allergy include atopic dermatitis, bronchial asthma, allergic rhinitis and other atopic diseases (sometimes referred to merely as 'atopy'), allergic contact dermatitis, pollinosis and urticaria. Of these, the pharmaceutical composition of the present invention is preferably used as an agent for preventing or treating pollinosis and atopic diseases (in particular atopic dermatitis).

Astragalin is capable of suppressing a rise in serum IgE level, and hence the pharmaceutical composition of the present invention can also be used for suppressing a rise in serum IgE level.

The serum IgE level suppressant of the present invention can be applied to all diseases accompanied by a rise in serum IgE level without limitation. Examples of diseases accompanied by a rise in serum IgE level include atopic dermatitis, bronchial asthma, allergic rhinitis, food allergies, pollinosis and urticaria.

The astragalin comprised in the pharmaceutical composition of the present invention may be synthesized, or may be from an astragalin-containing plant.

The pharmaceutical composition of the present invention comprises astragalin as an essential component together with suitable pharmaceutically acceptable carriers, and is used in the form of a usual pharmaceutical form.

The unit dosage form of the pharmaceutical composition can be selected from various forms in accordance with the therapeutic purpose. Typical examples include solid preparations such as tablets, pills, granules, capsules and troches; powdered preparations such as powders for internal use and powders for external use; liquid preparations such as solutions, suspensions, emulsions, injections (liquids, suspensions etc.), syrups, lotions, aerosols and ophthalmic solutions; cream-like preparations such as ointments; and cataplasms.

Examples of pharmaceutically acceptable carriers that may be used in the pharmaceutical composition of the present invention include binders, disintegrators, surfactants, absorption promoters, moisturizers, adsorbents, lubricants, fillers, extenders, humectants, and other diluents and excipients. Such carriers are selected in accordance with the unit dosage form to be obtained.

Moreover, if necessary, antiseptics, sweeteners, colorants, antioxidants, preservatives, aromatics, flavors and the like, and other medicines, can be incorporated into the pharmaceutical composition of the present invention during preparation.

The pharmaceutical composition can be prepared following conventional methods for the form to be made.

There are no particular limitations on the method of administering the pharmaceutical composition. The pharmaceutical composition is administered in accordance with the form thereof, for example orally in the case of tablets, pills, granules, capsules, troches, powders for internal use, solutions, suspensions, emulsions and syrups, and percutaneously in the case of powders for external use, lotions, ointments and cataplasms. An injection can be administered intravenously, intramuscularly, intracutaneously, subcutaneously or intraperitoneally. An aerosol can be administered nasally as a collunarium.

Another possible administration method is for a patient to wear a mask prepared, for example, by immersing a gauze mask in a liquid preparation or coating or spraying a gauze mask with a liquid preparation, and then drying. Such a mask is preferably worn for the purpose of preventing or treating pollinosis, especially during the pollen season. Yet another possible administration method is for a patient to wear rubber gloves or the like that have had a powdered preparation applied onto the inside thereof in advance.

The dosage of the pharmaceutical composition is suitably selected in accordance with conditions such as the form of the preparation, the age and sex of the patient and the severity of the disease, but is generally such that the daily intake of astragalin per kg of body weight is in a range of about 0.025 to 3 mg, preferably about 0.05 to 1.5 mg. The pharmaceutical composition may be administered either once per day or in 2 to 4 divided doses per day.

When the pharmaceutical composition of the present invention is used for preventing or treating pollinosis, it can, for example, be administered with the purpose of prevention to a person who has previously experienced pollinosis, starting a few weeks before the start of the pollen season.

3. External Preparation for Skin

The external preparation for skin of the present invention is capable of improving rough skin conditions, and hence can be used for improving rough skin conditions.

The external preparation for skin of the present invention can be used for preventing or treating skin diseases associated with type I allergy such as atopic dermatitis, allergic contact dermatitis and urticaria, and rough skin conditions accompanying such diseases.

The astragalin mixed into the external preparation for skin of the present invention may be synthesized, or may be from an astragalin-containing plant.

The astragalin content of the external preparation for skin of the present invention can be suitably selected from a wide range without limitation, so long as the intended effects are obtained. The astragalin content is preferably in a range of about 0.00001 to 80% relative to the total weight of the preparation, more preferably 0.0001 to about 70%.

The form of the external preparation for skin can be selected from various forms in accordance with the purpose. Specific examples include cleaning agents such as soaps, facial cleansers and shampoos, milky lotions, creams, emulsified preparations, ointments, other lotions, and preparations for use in the bath.

The external preparation for skin of the present invention comprises astragalin as an essential component, used together with suitable carriers in a conventional form for external preparation for skins.

Carriers used in the external preparation for skin of the present invention can be suitably selected from commonly used carriers in accordance with the form of the preparation. Such carriers include binders, surfactants, moisturizers, fillers, extenders, wetting agents, and other diluents and excipients.

Moreover, if necessary, antiseptics, colorants, preservatives, antioxidants, aromatics, and the like can be incorporated into the external preparation for skin of the present invention.

Moreover, crude drugs or herbs commonly mixed into external preparation for skins such as aloe, dokudami (*Houttuynia cordata*) and mugwort (*Artemisia vulgaris*) may also be mixed into the external preparation for skin of the present invention.

The external preparation for skin of the present invention can be prepared following conventional methods for the form to be made.

There are no particular limitations on the amount used of the external preparation for skin of the present invention, so long as the intended effects are obtained. A suitable amount as determined by the form of the preparation, the condition of the skin, the degree of skin roughness and so on may be applied to the skin once a day, or 2 to 4 times a day.

The external preparation for skin of the present invention may be used not only when the skin is already rough, but also to prevent rough skin by people prone to rough skin such as people with sensitive skin.

BEST MODE FOR CARRYING OUT THE INVENTION

The present invention will now be described in more detail through experimental examples and formulation examples. However, the scope of the invention is not limited to only these examples.

The experimental setup used in undermentioned Experimental Example 1 is a typical setup used for type I allergy screening. The action of astragalin of suppressing type I allergy was tested using this setup.

EXPERIMENTAL EXAMPLE 1

Suppression of Passive Cutaneous Anaphylaxis (PCA) in Mice

Ten 5-week-old ddY male mice were purchased from Japan SLC, and were reared at a room temperature of 23±3° C. and a humidity of 55±15%, with a 12 hour light-dark cycle (light period 7:00 to 19:00). The mice were kept 5 to a cage, and were fed a standard diet (Labo MR Stock, Nihon Nosan Kogyo K.K.) for a 7-day preliminary period, before being divided into a group to be administered astragalin and a control group each of 5 mice. A 0.025% (w/v) solution of astragalin in distilled water was forcedly orally administered (1.25 mg/5 ml/kg) to the astragalin-administered group using a metal stomach tube, while distilled water was forcedly orally administered (5 ml/kg) to the control group. One hour after the administration, 20 μl of an anti-DNP mouse IgE antibody (10 μg/ml) was intracutaneously injected into the right auricula and 20 μl of physiological saline into the left auricula of each mouse. 24 hours after the intracutaneous injections, 100 μl of DNP-BSA (1 mg/ml) was intravenously injected into the tail of each mouse. 15 minutes later, the thicknesses of the left and right auriculae of each mouse were measured three times using a thickness gauge (Ozaki Seisakusho K.K.). The auricula swelling rate was then calculated for each group using undermentioned equation 1, and the auricula swelling suppression rate was calculated using undermentioned equation 2. The measurement values were represented by the mean and standard deviation.

$$\text{Auricula swelling rate (\%)} = \frac{\text{Right auricula thickness} - \text{Left auricula thickness}}{\text{Left auricula thickness}} \times 100 \quad \text{(Eqn. 1)}$$

$$\text{Auricula swelling suppression rate (\%)} = 100 - \frac{\text{Mean auricula swelling rate for astragalin-administered group}}{\text{Mean auricula swelling rate for control group}} \times 100 \quad \text{(Eqn. 2)}$$

For the control group administered distilled water, the left auricula thickness was 0.270±0.017 mm, whereas the right auricula thickness had increased to 0.343±0.040 mm, giving an auricula swelling rate of 27.2±12.5%; for the astragalin-administered group, on the other hand, the left auricula thickness was 0.242±0.013 mm, whereas the right auricula thickness had increased to 0.286±0.017 mm, giving an auricula swelling rate of 18.2±5.0% (see FIG. 1). Auricula swelling was thus suppressed in the astragalin-administered group compared with in the control group, with the auricula swelling suppression rate being 33%.

Through Experimental Example 1, it was thus verified that astragalin has an action of suppressing type I allergy.

A type I allergic reaction is accompanied by release of chemical transmitters such as histamine from the sensitized mastocytes or basocytes. After verifying that astragalin has an action of suppressing type I allergy through Experimental Example 1, the present inventors thus conducted the following test to find out whether or not astragalin has an effect of suppressing histamine release.

EXPERIMENTAL EXAMPLE 2

Histamine Release Suppression Test Using Human Whole Blood

Human whole blood was collected from healthy volunteers and heparin was added thereto. A blood sample was prepared by adding 6 parts by weight of a histamine release buffer (Immunotech) to 1 part by weight of the whole blood to which the heparin had been added. 200 µl of the blood sample and 100 µl of a histamine release buffer comprising astragalin (33 µM), kaempferol (33 µM) or epinephrine (1638 µM or 4917 µM) were placed in an Eppendorf tube and allowed to stand for 30 minutes while cooling in ice (final concentration: 11 µM for astragalin, 11 µM for kaempferol, 546 µM or 1639 µM for epinephrine).

Centrifugal separation (3000 rpm, 5 minutes, 4° C.) was then carried out and the supernatant removed, and the resulting cells were again put into 300 µl of a histamine release buffer. 4.5 µl of 1 mg/ml CRA-1 (an anti human FcεRI receptor antibody, Cosmo Bio) was next added to the mixture (final CRA-1 concentration 15 µg/ml), and incubation was carried out for 30 minutes at 37° C. After centrifugation (3000 rpm, 10 minutes, 4° C.), the amount of histamine in the supernatant was measured using a histamine EIA kit (Immunotech). The histamine release suppression rate (%) was then calculated using undermentioned equation 3 from histamine amounts calculated from a calibration curve. The measurements were carried out with N=3, and the measurement values were represented by the mean and standard deviation.

$$\text{Histamine release suppression rate } (\%) = 100 - \frac{A-B}{C-B} \times 100 \quad \text{(Eqn. 3)}$$

A: Amount of histamine released from cells to which astragalin/kaempferol/epinephrine added (n mole)

B: Amount of histamine released from untreated cells (n mole)

C: Amount of histamine released from cells to which only CRA-1 added (n mole)

Figure 2:
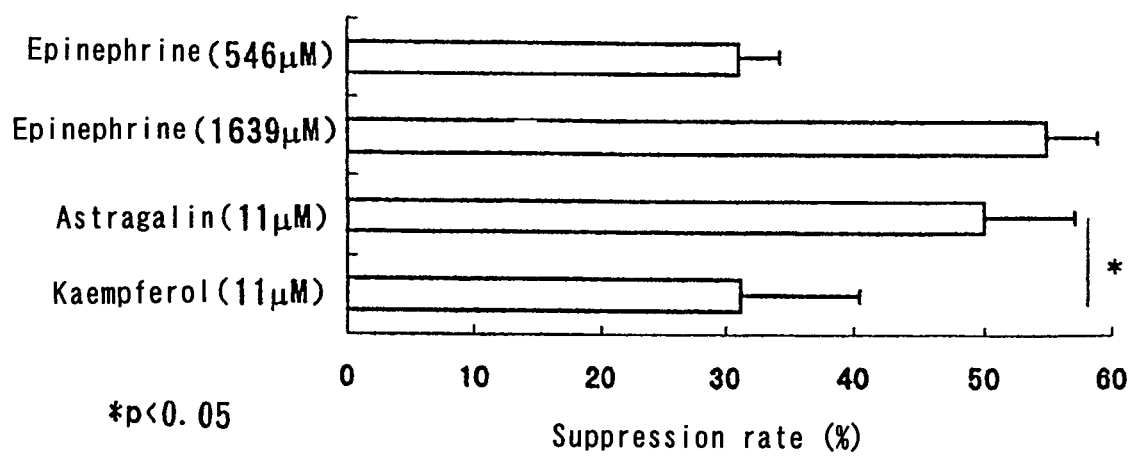
FIG. 2 shows the suppressive effect of astragalin on histamine release (Experimental Example 2)

The histamine release suppression results for astragalin, kaempferol and epinephrine are shown in FIG. 2. The histamine release suppression rate was 50±7% for astragalin (11 µM), and 31±9% for kaempferol (11 µM) The histamine release suppression rate for epinephrine, which is a medicine, was 31±3% at 546 µM and 55±4% at 1639 µM. It can thus be seen that astragalin (kaempferol-3-glucoside) suppresses histamine release significantly better than kaempferol, having a histamine release suppression action about the same as that of epinephrine of 150 times the concentration.

EXPERIMENTAL EXAMPLE 3

Intake Test Using NC/Nga Mice

NC/Nga mice are conventional grade animals, and atopic dermatitis model mice that spontaneously develop atopic dermatitis. Moreover, the development of atopy is accompanied by a rise in serum IgE level.

Ten 4-week-old NC/Nga male mice were purchased from Japan SLC, and were reared at a room temperature of 23±3° C. and a humidity of 55±15%, with a 12 hour light-dark cycle (light period 7:00 to 19:00). The mice were kept 5 to a cage, and were fed a standard diet (Labo MR Stock, Nihon Nosan Kogyo K.K.) for a 7-day preliminary period, before being divided into a control group and a group to be administered astragalin, each of 5 mice. The mice were then allowed to eat the following diets ad libitum. Control group: A diet prepared by adding a corn starch (0.0007%, Oriental Enzyme K.K.) to MF powder (Oriental Enzyme K.K.) and then mixing in a mixer.

Astragalin-administered group: A diet prepared by adding astragalin (0.0007%) to the MF powder and then mixing in a mixer.

It was observed with the naked eye whether or not the NC/Nga mice had developed atopic dermatitis at the start of the experiment (5 weeks old) and then 1-week intervals until the end of the experiment (13 weeks old). The following judgement criteria were used.

No dermal symptoms: 0

Slight inflammation or scratch wounds: 1

Medium degree inflammation, scratch wounds or bleeding: 2

Severe inflammation, scratch wounds or bleeding: 3

Figure 3:
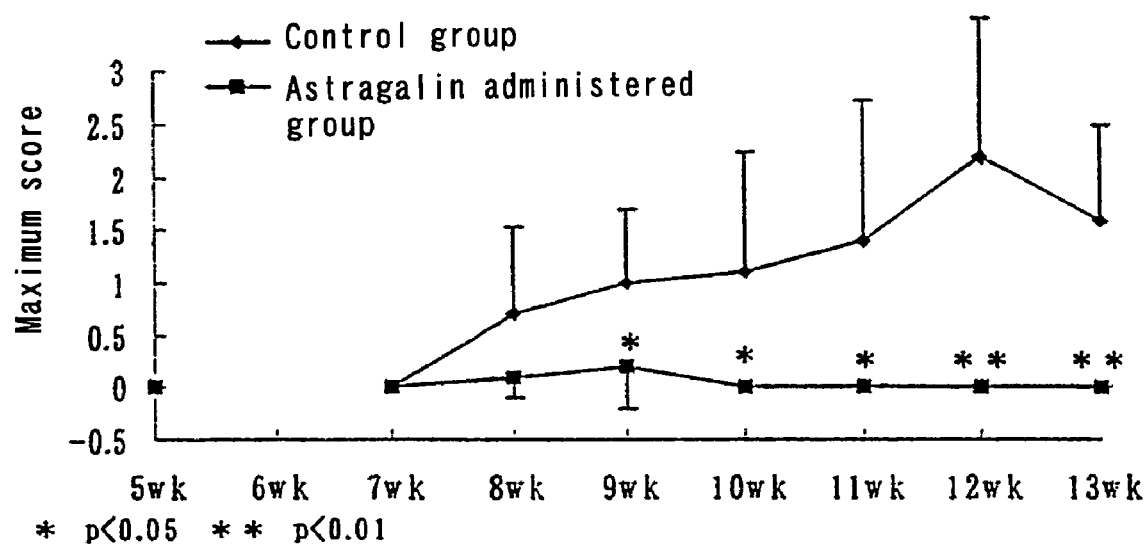
FIG. 3 shows changes over time in dermal symptoms in NC/Nga mice after administration of astragalin (Experimental Example 3)

For each mouse, the judgement was carried out for each of the head, the shoulders and the back, and then the highest of the three scores was taken as the 'maximum score'. The results are shown in FIG. 3 as the mean values of the maximum score for the two groups. In the control group, symptoms started to appear at 7 weeks old, 3 of the 5 mice had developed symptoms by 8 weeks old, and 4 of the 5 mice had developed symptoms by the end of the experiment (13 weeks old). In the astragalin-administered group, on the other hand, not one mouse had developed symptoms by the end of the experiment (13 weeks old).

Figure 4:
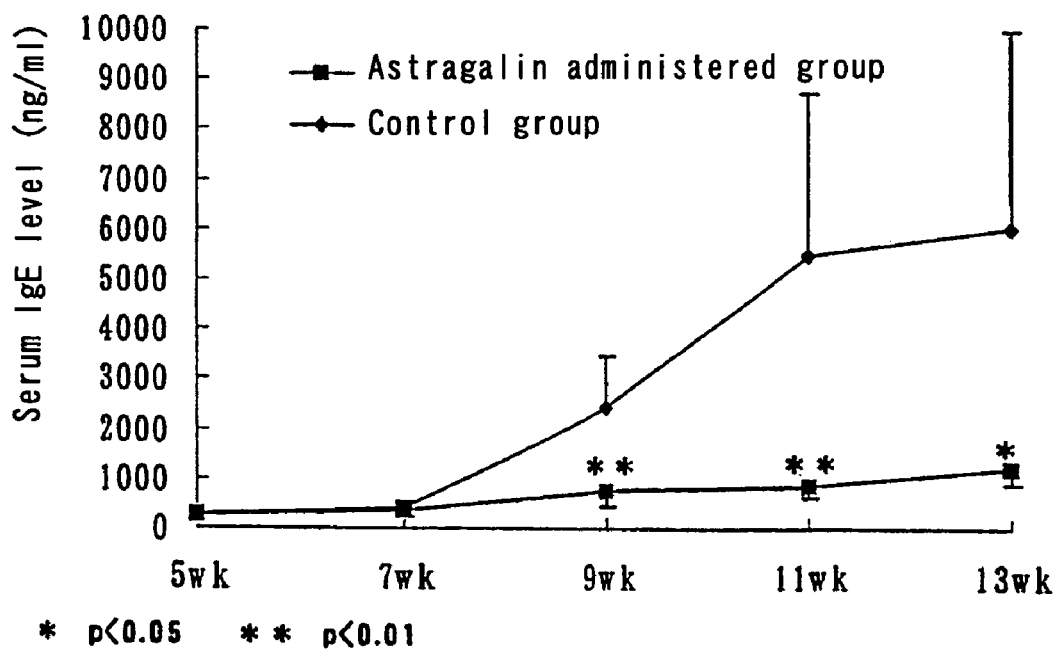
FIG. 4 shows changes over time in serum IgE level in NC/Nga mice after administration of astragalin (Experimental Example 4).

The serum IgE level was measured at the start of the experiment and then at 2-week intervals until the end of the experiment by collecting blood from the orbit and then using a mouse IgE measurement kit 'Yamasa' EIA (lot 702). The serum IgE level measurement values were represented by the mean and standard deviation. The differences between the two groups were tested for statistical significance using t-tests, and a significance level of 5% or less was determined significant. The results are shown in FIG. 4.

In both of the groups, the serum IgE level started to rise at age 7 weeks and then rose gradually with age. At the end of the experiment (13 weeks), however, the serum IgE level was 6,018 ng/ml for the control group but only 1,225 ng/ml for the astragalin-administered group, with the difference between the two being statistically significant, showing that the astragalin had suppressed the rise in serum IgE level.

It was thus verified that administering astragalin suppresses both the incidence rate of atopic dermatitis and the rise in serum IgE level.

EXPERIMENTAL EXAMPLE 4

Expression of IL-4 mRNA Using the RT-PCR

A human basophilic leukemia cell line (KU812) was cultured at 37° C. with 5% $CO_2$ in an RPMI 1640 culture medium (Gibco) containing 10% bovine fetal serum (treated at 56° C. for 30 minutes). The KU812 cells ($5 \times 10^5$ cells/ml) were then stimulated using astragalin (0, 1.1, 3.3 or 11 µM) and an A23187 ionophore (1 µM). After washing, the total RNA was collected using RNAzol (Biotex, USA). 500 ng of the collected total RNA was mixed with an RT mixture (Perkin Elmer Cetus, USA), and then incubation was carried out for 5 minutes at 99° C. followed by 60 minutes at 37° C. After the RT products had been obtained, PCR amplification was carried out using an IL-4-specific primer and β-actin-specific primer. The products were subjected to migration in 2% agarose gel and stained with ethidium bromide, and then the amount of expression was evaluated. As a result, it was found that the IL-4 expression of the basophilic leukemia was suppressed through administration of astragalin, with there being particularly marked effects when the concentration was 3.3 µM or 11 µM.

IL-4 is a Th2 cytokine that is involved in IgE production. The fact that suppression of IL-4 expression was observed thus shows that astragalin is involved in suppressing the rise in IgE level.

EXPERIMENTAL EXAMPLE 5

Thirteen volunteers who had previously experienced pollinosis were asked to drink 240 µg of astragalin (in the form of 1 ml of concentrated persimmon leaf extract) dissolved in a suitable amount (50 to 200 ml) of water or hot water twice a day (morning and evening) starting 14 days before the start of the pollen season and ending 14 days after the start of the pollen season.

Sneezing, nasal discharge, nasal congestion and extent of impediment to daily life were evaluated using a points system both during the 7 days immediately before stopping drinking the astragalin solution ('while drinking' below) and during the 7 days immediately after stopping drinking the astragalin solution ('after stopping drinking' below).

For sneezing, 1 point was recorded for each sneeze. For nasal discharge, 1 point was recorded each time the nose was blown. For nasal congestion, 3 points were recorded when the nose was completely blocked such that breathing through the nose was impossible, 2 points were recorded when the nose was blocked such that breathing through the nose was difficult, 1 point was recorded when the nose was slightly blocked, and 0 points were recorded when the nose was not blocked. For extent of impediment to daily life, 3 points were recorded when one could not settle down to work at all, 2 points were recorded when there was some impediment to working, 1 point was recorded when there was little impediment to working, and 0 points were recorded when there was no impediment to working; points were recorded daily.

The total point scores for the 7-day 'while drinking' period and the 7-day 'after stopping drinking' period are shown in Table 1 below as mean values over the 13 volunteers.

TABLE 1

|  | Sneezing | Nasal discharge | Nasal congestion | Impediment to daily life |
|---|---|---|---|---|
| While drinking | 23 ± 21 | 21 ± 26 | 3 ± 3 | 1 ± 2 |
| After stopping drinking | 68 ± 79 | 62 ± 83 | 13 ± 11 | 10 ± 10 |
| p value | 0.001 | 0.003 | 0.003 | 0.005 |

It can be seen that the point score for each of the symptoms increased after stopping drinking the astragalin solution compared with while drinking the astragalin solution. Various symptoms of pollinosis can thus be expected to be alleviated by ingesting astragalin.

Two of the volunteers had a rough skin condition before treatment in the form of administration of the astragalin solution by drinking, but the condition improved while drinking the astragalin solution. Rough skin conditions can also be expected to be improved upon applying astragalin to the skin in the form of a cosmetic.

Formulation examples are given below. Each of the formulations can be prepared following conventional methods for the form to be made.

Formulation Example 1: Chewable tablet

|  | (mg) |
|---|---|
| Astragalin | 5 |
| Xylitol | 300 |
| Aspartame | 4 |
| Magnesium stearate | 10 |
| Aromatic | 1 |

Formulation Example 2: Chewing gum

|  | (g) |
|---|---|
| Gum base | 20 |
| Powdered sugar | 60.5 |
| Starch syrup | 18 |
| Aromatic | 1 |
| Astragalin | 0.5 |
| Total | 100 |

Formulation Example 3: Ice cream

|  | (g) |
|---|---|
| Concentrated milk | 30 |
| Fresh cream | 30 |
| Sugar | 18 |
| Emulsifier | 0.3 |
| Stabilizer | 0.5 |
| Aromatic | 0.3 |
| Egg extract | 1 |

-continued

Formulation Example 3: Ice cream

| | (g) |
|---|---|
| Astragalin | 0.5 |
| Water | 19.4 |
| Total | 100 |

Formulation Example 4: Chocolate

| | (g) |
|---|---|
| Cacao mass | 22 |
| Whole milk powder | 10 |
| Cacao butter | 19.9 |
| Lactose | 5 |
| Sugar | 40 |
| Aromatic | 0.1 |
| Egg extract | 1 |
| Astragalin | 2 |
| Total | 100 |

What is claimed is:

1. A method for treating human pollinosis in a subject, comprising: administering kaempferol-3-glucoside in an effective amount to a subject who suffers from pollinosis.

2. The method of claim 1, wherein said subject has previously experienced pollinosis.

3. The method of claim 1, wherein said administering begins before the start of the pollen season.

4. The method of claim 1, wherein the administration is orally, in chewable tablet form.

5. The method of claim 1, wherein the administration is orally, in liquid form.

6. The method of claim 1 wherein the administration is selected from the group consisting of orally, intravenously, topically, intramuscularly, intracutaneously, subcutaneously, intraperitoneally, and by aerosolization.

7. The method of claim 6, wherein the administration is orally, admixed with a food product.

8. The method of claim 7, wherein the food product is selected from the group consisting of: juice, soft drinks, teas, powdered soups, jelly, cookies, biscuits, cereal, crackers, candy, breads, noodles, fish paste, chewing gum, ice cream, and chocolate.

9. The method of claim 1 wherein the administration is between one and 4 doses per day.

10. A method for treating human pollinosis in a subject, comprising: administering kaempferol-3-glucoside in an amount of about 0.48 mg per day per adult to about 2 g per day per adult to a subject who suffers from pollinosis.

11. The method of claim 10 wherein the administration is selected from the group consisting of orally, intravenously, topically, intramuscularly, intracutaneously, subcutaneously, intraperitoneally, and by aerosolization.

12. The method of claim 11, wherein the administration is orally, admixed with a food product.

13. The method of claim 12, wherein the food product is selected from the group consisting of: juice, soft drinks, teas, powdered soups, jelly, cookies, biscuits, cereal, crackers, candy, breads, noodles, fish paste, chewing gum, ice cream, and chocolate.

14. The method of claim 10 wherein the administration is between one and 4 doses per day.

15. A method for treating human pollinosis in a subject, comprising: administering kaempferol-3-glucoside in an amount of about 0.025 to about 3 mg per day per kg of body weight to a subject who suffers from pollinosis.

16. The method of claim 15, wherein said kaempferol-3-glucoside is administered in an amount of about 0.05 to about 1.5 mg per day per kg of body weight to a subject who suffers from pollinosis.

17. The method of claim 15 wherein the administration is selected from the group consisting of orally, intravenously, topically, intramuscularly, intracutaneously, subcutaneously, intraperitoneally, and by aerosolization.

18. The method of claim 17, wherein the administration is orally, admixed with a food product.

19. The method of claim 18, wherein the food product is selected from the group consisting of: juice, soft drinks, teas, powdered soups, jelly, cookies, biscuits, cereal, crackers, candy, breads, noodles, fish paste, chewing gum, ice cream, and chocolate.

20. The method of claim 15 wherein the administration is between one and 4 doses per day.

* * * * *

UNITED STATES PATENT AND TRADEMARK OFFICE
CERTIFICATE OF CORRECTION

PATENT NO.         : 7,211,567 B1
APPLICATION NO.    : 09/937365
DATED              : May 1, 2007
INVENTOR(S)        : Mayumi Kotani et al.

Page 1 of 1

It is certified that error appears in the above-identified patent and that said Letters Patent is hereby corrected as shown below:

On Title Page, item [54] and Column 1, in Title section, please delete "COMPOSITION" and insert --COMPOSITIONS--, therefor.

On Title Page, at Column 2, in Other Publications section, please delete "L.)," and insert --L.,--, therefor.

At Column 1, Lines 59-60, please delete "The present invention thus provides the items listed below." and insert the same on Line 60 as a new paragraph.

Signed and Sealed this

Twelfth Day of August, 2008

JON W. DUDAS
*Director of the United States Patent and Trademark Office*